United States Patent [19]

Hashimoto

[11] 4,066,454

[45] * Jan. 3, 1978

[54] ELECTROPHOTOGRAPHIC LIGHT-SENSITIVE MATERIAL CONTAINING INDENOTHIOPHENONE OR ITS DERIVATIVE AND PROCESS OF PREPARING INDENOTHIOPHENONE AND ITS DERIVATIVE

[75] Inventor: Mitsuru Hashimoto, Tokyo, Japan

[73] Assignee: Kabushiki Kaisha Ricoh, Tokyo, Japan

[ * ] Notice: The portion of the term of this patent subsequent to Mar. 18, 1975, has been disclaimed.

[21] Appl. No.: 619,508

[22] Filed: Oct. 3, 1975

Related U.S. Application Data

[62] Division of Ser. No. 416,792, Nov. 19, 1973, abandoned.

[51] Int. Cl.² .............................................. G03G 5/06
[52] U.S. Cl. ...................................... 96/1.5 R; 96/1.6
[58] Field of Search ................................... 96/1.5, 1.6

[56] References Cited

U.S. PATENT DOCUMENTS

| | | | |
|---|---|---|---|
| 3,287,122 | 11/1966 | Hoegl | 96/1.5 |
| 3,311,471 | 3/1967 | Hepher | 96/1.5 |
| 3,408,190 | 10/1968 | Mammino | 96/1.5 |
| 3,871,883 | 3/1975 | Hashimoto | 96/1.6 X |
| 3,905,814 | 9/1975 | Crommentuyn et al. | 96/1.5 |

*Primary Examiner*—David Klein
*Assistant Examiner*—John L. Goodrow
*Attorney, Agent, or Firm*—Cooper, Dunham, Clark, Griffin & Moran

[57] ABSTRACT

Electrophotographic light-sensitive materials having a photoconductive layer formed on an electroconductive support, the photoconductive layer comprising an organic photoconductive compound (monomer or polymer) and indenothiophenone or its derivative as a sensitizer, and a process of preparing indenothiophenone and its derivatives from a benzoic acid derivative and a thiophene derivative.

4 Claims, No Drawings

ELECTROPHOTOGRAPHIC LIGHT-SENSITIVE MATERIAL CONTAINING INDENOTHIOPHENONE OR ITS DERIVATIVE AND PROCESS OF PREPARING INDENOTHIOPHENONE AND ITS DERIVATIVE

This is a division of application Ser. No. 416,792 filed Nov. 19, 1973 now abandoned.

BACKGROUND OF THE INVENTION

Electrophotographic light-sensitive materials comprise an electroductive support with a photoconductive layer formed thereon. The principle of an electrophotographic process is that an electrostatic latent image is produced by image-wise exposure of a charged photoconductive layer and the image is then developed by a developer or toner (in liquid or powder form) which is electrically precipitated on the latent image to form a visible image. Conventionally, for forming the photoconductive layer, inorganic photoconductors such as photoconductive zinc oxide or selenium are used. Recently, the use of an organic photoconductive compound e.g. a photoconductive polymer such as poly-N-vinylcarbazole in place of the inorganic photoconductors has been proposed. Amongst the advantages of organic photoconductive compounds are transparency and mechanical flexibility. Additionally, they are easy to form into photoconductive layers. On the other hand, they absorb light in the ultraviolet region of the spectrum, but are not sensitive to visible light. To overcome this disadvantage, i.e. to shift their absorption into the visible region of the spectrum, dyestuff sensitizers are added to the organic photoconductive compounds. Such dyestuffs as have been previously employed are generally not stable and bleach out quickly so that the organic photoconductive compounds lose their sensitivity in the visible region. As a result, electrophotographic light-sensitive materials prepared utilizing organic photoconductive compounds containing dyestuff sensitizers are of limited practical use.

It is, therefore, an object of the present invention to provide stable sensitizers and an improved electrophotographic light-sensitive product containing such stable sensitizers.

SUMMARY OF THE INVENTION

The present invention relates to electrophotographic light-sensitive materials having a photoconductive layer formed on an electroconductive support, the photoconductive layer comprising an organic photoconductive compound such as a photoconductive monomer or polymer and indenothiophenone or a derivative thereof as a sensitizer, and a process of preparing indenothiophenone and its derivatives.

In general, electrophotographic light-sensitive material comprises an electroconductive support and a photoconductive layer formed on the support.

The electrophotographic light-sensitive materials of the present invention are characterized in that the photoconductive layer comprises an organic photoconductive compound sensitized with indenothiophenone or a nitrated derivative thereof of the following general formulas, i.e. indenothiophenone or its derivatives are used as sensitizer for the organic photoconductive compound.

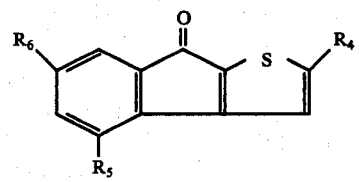

(A)

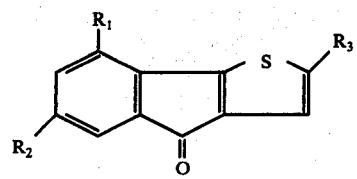

(B)

wherein $R_1$, $R_2$, $R_3$, $R_4$, $R_5$ and $R_6$ are hydrogen or nitro groups.

These compounds are respectively designated as follows:

A 8H-indeno[2,1-b]thiophen-8-one
B 4H-indeno[1,2-b]thiophen-4-one and nitrated derivatives thereof.

The electrophotographic light-sensitive materials of the present invention are prepared by forming a photoconductive layer on an electroconductive support, the photoconductive layer comprising any of a variety of organic photoconductive monomers such as N-vinylcarbazole or organic photoconductive polymers such as poly-N-vinylcarbazole and indenothiophenone or its nitro substituted derivative. Indenothiophenone or its derivative are typically utilized in an amount of from 0.01 to 1.2 moles, preferably from 0.1 to 1 mole per mole of the organic photoconductive monomer or per monomeric unit of the organic photoconductive polymer (monomeric unit of an organic photoconductive polymer represents 1 mole of the polymer).

Indenothiophenone and its derivatives for use in accordance with the present invention are shown by structural formulas as follows:

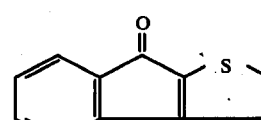

8H-indeno[2,1-b]thiophen-8-one (I)

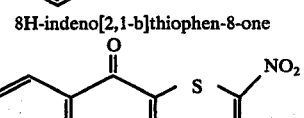

2-nitro-8H-indeno[2,1-b]thiophen-8-one (II)

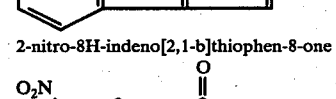

6-nitro-8H-indeno[2,1-b]thiophen-8-one (III)

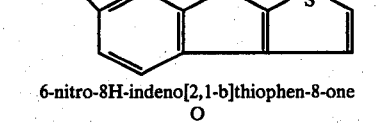

2,6-dinitro-(H-indeno[2,1-b]thiophen-8-one (IV)

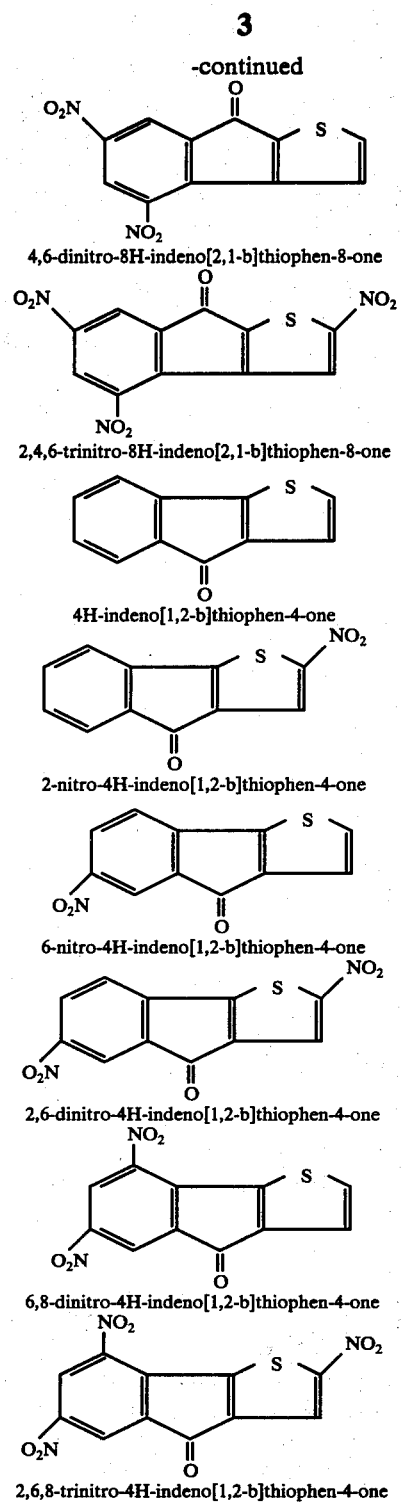

-continued 4,6-dinitro-8H-indeno[2,1-b]thiophen-8-one (V)

2,4,6-trinitro-8H-indeno[2,1-b]thiophen-8-one (VI)

4H-indeno[1,2-b]thiophen-4-one (VII)

2-nitro-4H-indeno[1,2-b]thiophen-4-one (VIII)

6-nitro-4H-indeno[1,2-b]thiophen-4-one (IX)

2,6-dinitro-4H-indeno[1,2-b]thiophen-4-one (X)

6,8-dinitro-4H-indeno[1,2-b]thiophen-4-one (XI)

2,6,8-trinitro-4H-indeno[1,2-b]thiophen-4-one (XII)

Organic photoconductive compounds for use in accordance with the present invention are as follows:

Preferred organic photoconductive polymers include poly-N-vinylcarbazole, chlorinated or brominated poly-N-vinylcarbazole, polyvinylpyrene, polyvinylnaphthalene, polyvinylanthracene, poly-9-vinylfluorene, poly-1-arylimidazole and poly-P-phenylene-1,3,4-oxadiazole.

Preferred organic photoconductive monomers include N-vinylcarbazole, N-ethylcarbazole, anthracene and pyrene.

However, poly-N-vinylcarbazole and chlorinated or brominated poly-N-vinylcarbazole are preferably used as an organic photoconductive compound.

Suitable electroconductive supports which may be used in the present invention include, for example, metallic sheets such as aluminium foil and synthetic resin sheets coated with a layer of aluminium.

Electrophotographic light-sensitive materials in accordance with the present invention can be produced, for example, as follows:

From about 0.1 to about 1 mole of indenothiophenene or its derivative is mixed with 1 mole of the organic photoconductive monomer or monomeric unit of the organic photoconductive polymer and the mixture is dissolved in an organic solvent such as tetrahydrofuran or dioxane to prepare a light-sensitive solution. Polyester resin, novolak resin or acrylic resin may, if desired, be added to this solution. Furthermore, polychlorobiphenyl may be added to this solution. The resulting light-sensitive solution can then be applied to a surface of an electroconductive support, for example, using a doctor blade, left to set, and then dried.

The following Examples are given by way of illustration only. In the Examples, 6,8-dinitro-4H-indeno[1,2-b]thiophen-4-one having Formula XI or 2,6,8-trinitro-4H-indeno[1,2-b]thiophen-4-one having Formula XII is used as a sensitizer:

EXAMPLE 1

A light-sensitive solution containing a photoconductive composition for use in the production of a photoconductive layer was prepared from the following ingredients:

| | | |
|---|---|---|
| poly-N-vinylcarbazole | 387 mg | (2m moles) |
| 6,8-dinitro-4H-indeno [1,2-b]thiophen-4-one | 55 mg | (0.2m mole) |
| Polyester Adhesive 49000 (Trade mark of polyester resin sold by E. I. Du Pont de Nemours & Co., Inc.) | 38 mg | |
| tetrahydrofuran | 6.4 g | |

This light-sensitive solution was applied as a coat on an aluminium layer on a polyester resin film (thickness: 75μ), using a doctor blade set at a 200μ gap, and then dried in a desiccator holding silica gel to evaporate a solvent, and further dried at a temperature of 60° C for about 10 minutes and at a temperature of 120° C for about 2 minutes. A photoconductive layer having a thickness of 13μ to 14μ was formed on the aluminium layer.

The sensitivity of the electrophotographic light-sensitive material (No. 1) of the present invention thus obtained was evaluated as follows:

The material obtained above was divided into two parts. The photoconductive layer was negatively or positively charged by a corona discharge of about −6 kV (discharge current: 6μ Amp) or +6 kV (discharge current: 4μ Amp) for 20 seconds to obtain a surface electric potential Vdo and then subjected to dark decay for 20 seconds to obtain a surface residual potential Vpo. This charged light-sensitive material was exposed to a tungusten filament lamp whose illuminance at the surface of the light-sensitive layer was adjusted to be 20 lux. The time (seconds) required to reduce the surface electric potential to one half or one fifth of the residual surface potential Vpo were measured by using rotary sector type electrometer. The amounts of exposure, El/2 (lux.sec) and El/5 (lux.sec), required to reduce the surface electric potential to one half and one fifth of Vpo are calculated by "20 lux × time (seconds)". The El/2 and El/5 represent the sensitivity of the electrophotographic light-sensitive material. The lower the value of El/2 or El/5 the higher the sensitivity of the light-sensitive material. The values of Vdo, Vpo, El/2 and El/5 are shown in the Table 1 below.

Table 1

| Charge | Vdo (V) | Vpo (V) | El/2 (lux·sec) | El/5 (lux·sec) |
|---|---|---|---|---|
| − | 1030 | 770 | 26.0 | 72.3 |
| + | 960 | 790 | 19.7 | 49.7 |

EXAMPLES 2–5

Electrophotographic light-sensitive material (No. 2 – No. 5) of the present invention were obtained by repeating the same procedure as that of Example 1 except that poly-N-vinylcarbazole, Polyester Adhesive 49000, tetrahydrofuran 6,8-dinitro-4H-indeno[1,2-b]thiophen-4-one and 2,6,8-trinitro-4H-indeno[1,2-b]thiophen-4-one were used in an amount as shown in the following Table 2.

Table 2

| | poly-N-vinyl-carbazole | 6,8-dinitro-4H-indeno[1,2-b]thiophen-4-one | Polyester Adhesive 49000 | tetrahydrofuran |
|---|---|---|---|---|
| No. 2 | 387 mg (2m moles) | 276 mg (1m mole) | 58 mg | 8.3 g |
| No. 3 | " 387 mg (2m moles) | 2,6,8-trinitro-4H-indeno[1,2-b]thiophen-4-one 64 mg (0.2m mole) | " 39 mg | " 6.5 g |
| No. 4 | " 193 mg (1m mole) | 160 mg (0.5m mole) | 30 mg | 2.2 g |
| No. 5 | " 193 mg (1m mole) | 321 mg (1m mole) | 45 mg | 4.1 g |

Vdo, Vpo, El/2 and El/5 of the light-sensitive materials No. 2 – No. 5 were measured by repeating the same procedure as that of Example 1. The values obtained are shown in the Table 3 below.

Table 3

| No | charge | Vdo (V) | Vpo (V) | El/2 (lux·sec) | El/5 (lux·sec) |
|---|---|---|---|---|---|
| 2 | − | 710 | 560 | 15.7 | 31.4 |
|   | + | 670 | 450 | 15.4 | 44.3 |
| 3 | − | 880 | 610 | 16.9 | 48.0 |
|   | + | 800 | 640 | 12.9 | 34.6 |
| 4 | − | 840 | 510 | 10.3 | 34.3 |
|   | + | 740 | 280 | 12.6 | 36.6 |
| 5 | − | 990 | 640 | 9.7 | 29.1 |
|   | + | 720 | 390 | 25.4 | 73.4 |

EXAMPLES 6–9

Electrophotographic light-sensitive materials No. 6 – No. 9 were obtained by repeating the same procedure as that of Example 1 except that chlorinated or brominated poly-N-vinylcarbazole, Polyester Adhesive 49000, tetrahydrofuran and 2,6,8-trinitro-4H-indeno[1,2-b]thiophen-4-one were used in an amount as shown in the following Table 4.

Table 4

| | *1) chlorinated poly-N-vinyl-carbazole | 2,6,8-trinitro-4H-indeno[1,2-b]thiophen-4-one | Polyester Adhesive 4900 | tetrahydrofuran |
|---|---|---|---|---|
| No. 6 | | | 48 mg | 4.4 g |

Table 4-continued

| | | | | |
|---|---|---|---|---|
| No. 7 | 228 mg (1m mole) " | 321 mg (1m mole) " | " | " |
| No. 8 | 228 mg (1m mole) *2) brominated poly-N-vinyl-carbazole | 161 mg (0.5 m mole) " 321 mg (1m mole) | 34 mg " 48 mg | 3.6 g " 4.4 g |
| No. 9 | 233 mg (1m mole) " 233 mg (1m mole) | " " 161 mg (0.5m mole) | " " 34 mg | " " 3.1 g |

*1) Chlorine is contained in a proportion of one chlorine atom per monomeric unit of poly-N-vinylcarbazole.

*2) Bromine is contained in a proportion of one bromine atom per two monomeric units of poly-N-vinylcarbazole.

Vdo, Vpo, El/2 and El/5 of the light-sensitive materials No. 6 – No. 9 were measured by repeating the same procedure as that of Example 1. In this case, the light-sensitive materials were only negatively charged. The values ontained are shown in the Table 5 below.

Table 5

| No | charge | Vdo (V) | Vpo (V) | El/2 (lux·sec) | El/6 (lux·sec) |
|---|---|---|---|---|---|
| 6 | − | 790 | 560 | 9.1 | 32.0 |
| 7 | − | 910 | 680 | 10.3 | 35.1 |
| 8 | − | 1080 | 760 | 10.6 | 33.5 |
| 9 | − | 1170 | 860 | 13.4 | 35.5 |

In the Examples supra, only 6,8-dinitro-4H-indeno[1,2-b]thiophen-4-one and 2,6,8-trinitro-4H-indeno[1,2-b]thiophen-4-one were used as a sensitizer. However, the values of Vdo, Vpo, El/2 and El/5 similar to those as shown in the Tables 1, 3 and 5 can be obtained by using indenothiophenone or its derivatives as shown in Formulas I – X in place of the above-mentioned two indenothiophenone derivatives in an amount of from 0.1 mole per monomeric unit of poly-N-vinylcarbazole, or chlorinated or brominated poly-N-vinylcarbazole.

Electrophotographic light-sensitive materials having sensitivity to visible light can be produced with an organic photoconductive compounds having no sensitivity to visible light by adding a certain amount of indenothiophenone or its derivatives to said organic photoconductive compounds.

4H-indeno[1,2-b]thiophen-4-one and its derivatives having the following general formula are novel:

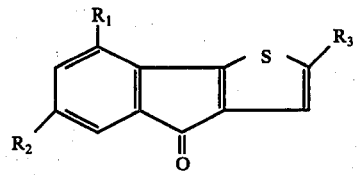

wherein $R_1$, $R_2$ and $R_3$ are hydrogen atom or nitro group.

Such indenothiophenone or its derivatives can be prepared by the process as described below.

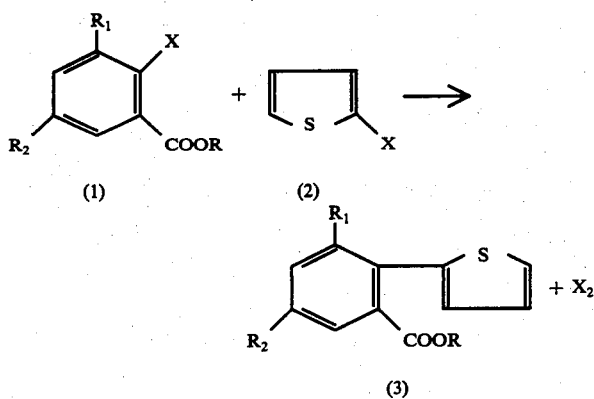

wherein $R_1$ and $R_2$ are hydrogen atom or nitro group, X is chlorine, bromine or iodine and R is a lower alkyl group of from 1 to 4 carbon atoms.

The reaction as shown above is carried out in an organic solvent such as dimethylformamide at a temperature of from 50° C to 150° C.

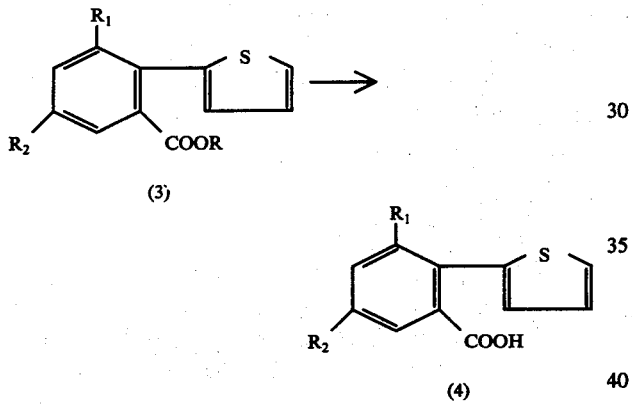

wherein $R_1$, $R_2$ and R are same as mentioned above.

The reaction as shown above is carried out in an aqueous solution of NaOH at a temperature of from 15° C to 60° C.

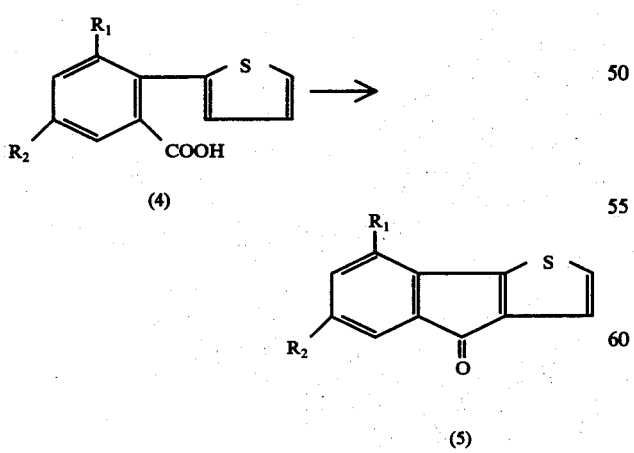

The reaction of ring closure as shown above is carried out in the presence of polyphosphoric acid at a temperature of from 70° C to 150° C.

The nitration as shown above is carried out in the presence of conc. $H_2SO_4$ at a temperature of from 0° C to 15° C.

The novel compound having nitro group of Formula (6) can alternatively be obtained by the following reaction process.

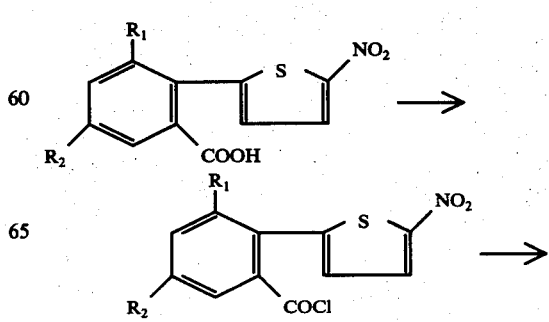

The last step of the reaction as shown above may be carried out as follows:

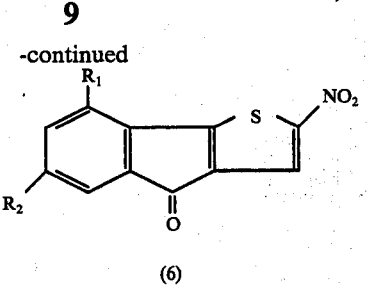

(6)

The novel compound of the present invention as shown above is most useful as a sensitizer for organic photoconductive compounds such as poly-N-vinylcarbazole.

The processes of preparing 6,8-dinitro-4H-indeno[1,2-b]thiophen-4-one (Formula XI) and 2,6,8-trinitro-4H-indeno[1,2-b]thiophen-4-one (Formula XII) are shown in detail below: 13g (0.05 mole) of methyl 2-chloro-3,5-dinitrobenzoate (m.p. 193° – 195° C, Formula 1 as shown above) and 21 g (0.1 mole) of 2-iodothiophene (b.p. 71° – 73° C at 15 mm Hg, Formula 2) were dissolved in 100 ml of dimethylformamide and the solution was heated at a temperature of 70° C. To this solution was added 20 g of active copper powder (as prepared by the method disclosed in Journal of American Chemical Society Vol. 55 Page. 4219 (1933) by E. C. Kleiderer and R. Adams) over 10 minutes and the solution was stirred at a temperature of 70° C for 50 minutes. After has been cooled, the reaction product was poured into 500 ml of cold water. The precipitate thus produced was filtered off and washed with water. After water was removed from the precipitate, the precipitate was added to 500 ml of acetone. After the stirring has been continued, the solution was filtered. The filtrate was treated with active carbon, and then filtered. The filtrate was condensed to obtain a crude product. 13.1 g of a yellowish crystalline product (m.p. 134° – 135° C) was obtained in a 85% yield by recrystallization of the crude product from ethyl alcohol. This product was identified to be methyl 2-α-thienyl-3,5-dinitrobenzoate (Formula 3) by ultimate analysis.

Analysis:

| | C(%) | H(%) | N(%) | S(%) |
|---|---|---|---|---|
| Calculated for $C_{12}H_8N_2O_6S$ | 46.75 | 2.61 | 9.09 | 10.41 |
| Found | 46.86 | 2.60 | 9.02 | 10.61 |

The presence of carbonyl group was proved by infrared absorption spectrum at 1730 cm$^{-1}$.

23.6 g of methyl 2-α-thienyl-3,5-dinitrobenzoate (Formula 3) thus obtained was dissolved in 100 ml of dioxane and to this solution was added an aqueous solution of NaOH (6 g of NaOH in 200 ml of water) and the stirring was continued for 3 hours. To this solution was added a small amount of active carbon and the solution was filtered. To the filtrate was added a cold water and the filtrate was neutralized with 6H-HCl with cooling to obtain a yellowish crystalline product. The crystalline product was filtered off and washed with water, and then dried. A crude product (m.p. 171° – 172° C) was obtained in a yield of 215 g. A yellowish crystalline product (m.p. 172.5° – 173.5° C) was obtained by the recrystallization of the crude product from benzene. This product was identified to be 2-α-thienyl-3,5-dinitrobenzoic acid (Formula 4) by ultimate analysis.

Analysis:

| | C(%) | H(%) | N(%) | S(%) |
|---|---|---|---|---|
| Calculated for $C_{11}H_6N_2O_6S$ | 44.90 | 2.06 | 9.52 | 10.90 |
| Found | 44.65 | 2.10 | 9.65 | 10.72 |

The presence of carbonyl group and hydroxyl group were respectively proved by infrared absorption spectrum at 1730 cm$^{-1}$ and 3000 cm$^{-1}$.

To 2 g of 2-α-thienyl-3,5-dinitrobenzoic acid (Formula 4) was added 60 g of polyphosphoric acid and the mixture was heated at a temperature of from 130° C to 140° C. After colling, the reaction mixture was poured into 200 ml of cold water. The precipitate thus produced was filtered off and washed with an aqueous solution of sodium carbonate and water, and then dried. 1.8 g of crude product (m.p. 206° – 207.5° C) was obtained in a 95% yield. An orange-brownish crystalline product (m.p. 209.5° – 210.0° C) was obtained by the recrystallization of the crude product from tetrahydrofuran. This product was identified to be a novel compound of 6,8-dinitro-4H-indeno[1,2-b]thiophen-4-one (Formula XI) by ultimate analysis.

Analysis:

| | C(%) | H(%) | N(%) | S(%) |
|---|---|---|---|---|
| Calculated for $C_{11}H_4N_2O_5S$ | 47.83 | 1.46 | 10.11 | 11.61 |
| Found | 47.65 | 1.57 | 10.01 | 11.62 |

The presence of carbonyl group was proved by infrared absorption spectrum at 1730 cm$^{-1}$.

1.5 g 6,8-dinitro-4H-indeno[1,2-b]thiophen-4-one (Formula XI) was dissolved in 30 ml of conc. $H_2SO_4$ and to this solution was added drop-wise with stirring, 5 ml of $HNO_3$ (S.G. 1.38), at a temperature of from 5° C to 10° C, over 30 minutes. Stirring was continued at this temperature for 1.5 hours. This solution was poured into 200 ml of cold water. A yellowish crystalline product separated from the solution. The crude product was filtered and washed with water and then dried. 1.4 g of a yellowish needle-like crystalline product (m.p. 233° – 223.5° C) was obtained in a 80.5% yield by the recrystallization of the crude product from dioxane-ethyl alcohol. This product was identified to be a novel compound of 2,6,8-trinitro-4H-indeno[1,2-b]thiophen-4-one (Formula XII) by ultimate analysis.

Analysis:

| | C(%) | H(%) | N(%) | S(%) |
|---|---|---|---|---|
| Calculated for $C_{11}H_3N_3O_7S$ | 41.16 | 0.93 | 13.08 | 9.98 |
| Found | 40.90 | 1.32 | 12.90 | 10.23 |

The presence of carbonyl group was proved by infrared absorption spectrum at 1730 cm$^{-1}$.

Derivatives of 8H-indeno[2,1-b]thiophen-8-one are disclosed in the following literatures:

D. W. H. MacDowell and Timothy B. Patrick; Journal of Organic Chemistry 32(8) 2441 – 2445 (1967)

Rene Dabard and Jean Y. Le Bihan; C.R. Adademy Science Ser. C. 271(4) 311 – 313 (1970).

I claim:

1. An electrophotographic light-sensitive material having a photoconductive layer formed on an electroconductive support, the photoconductive layer comprising a photoconductive material selected from the group consisting of organic photoconductive monomers and organic photoconductive polymers, and from 0.01 to 1.2 mole per mole of organic photoconductive monomer or per monomeric unit of the organic photoconductive polymer of indenothiophenone or a derivative thereof of the formulas:

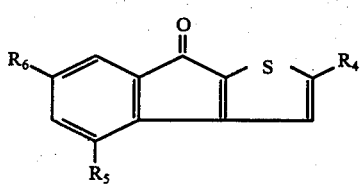

-continued

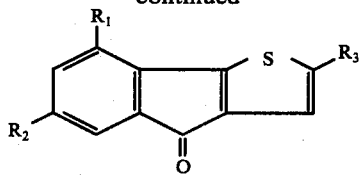

wherein $R_1$, $R_2$, $R_3$, $R_4$, $R_5$ and $R_6$ are hydrogen or nitro groups.

2. An electrophotographic light-sensitive material according to claim 1 wherein
   indenothiophenone or its derivative is present in an amount of from 0.1 to 1 mole per mole of the organic photoconductive monomer or per monomeric unit of the organic photoconductive polymer.

3. An electrophotographic light-sensitive material according to claim 1 wherein
   the indenothiophenone derivative is 6,8-dinitro-4H-indeno[1,2-b]thiophen-4-one.

4. An electrophotographic light-sensitive material according to claim 1 wherein
   the indenothiophenone derivative is 2,6,8-trinitro-4H-indeno[1,2-b]thiophen-4-one.

* * * * *